(12) United States Patent
Miura et al.

(10) Patent No.: US 7,394,096 B2
(45) Date of Patent: Jul. 1, 2008

(54) FIELD EFFECT TRANSISTOR AND METHOD OF MANUFACTURING THE SAME

(75) Inventors: Daisuke Miura, Numazu (JP);
Tomonari Nakayama, Yokohama (JP);
Toshinobu Ohnishi, Yokohama (JP);
Makoto Kubota, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/892,326

(22) Filed: Aug. 22, 2007

(65) Prior Publication Data

US 2008/0048185 A1 Feb. 28, 2008

Related U.S. Application Data

(62) Division of application No. 10/545,398, filed as application No. PCT/JP2004/12044 on Aug. 17, 2004, now Pat. No. 7,285,441.

(30) Foreign Application Priority Data

Aug. 28, 2003 (JP) ............................ 2003-305487

(51) Int. Cl.
*H01L 51/30* (2006.01)
*C07D 471/00* (2006.01)

(52) U.S. Cl. ................. 257/40; 257/E51.041

(58) Field of Classification Search ............... 257/40, 257/E51.041; 438/99; 540/145
See application file for complete search history.

(56) References Cited

U.S. PATENT DOCUMENTS

| 4,108,863 | A | 8/1978 | Komai et al. ............... 540/141 |
| 4,882,250 | A | 11/1989 | Liu et al. ................. 430/58.15 |
| 5,134,048 | A | 7/1992 | Terrell et al. ................. 430/58 |
| 5,248,336 | A | 9/1993 | Gerson et al. ............... 106/411 |
| 5,596,208 | A | 1/1997 | Dodabalapur et al. ......... 257/66 |
| 6,278,127 | B1 | 8/2001 | Dodabalapur et al. ......... 257/40 |
| 7,026,231 | B2 | 4/2006 | Kubota et al. ............... 438/586 |
| 7,094,625 | B2 | 8/2006 | Miura et al. ................. 438/99 |
| 2003/0226996 | A1 | 12/2003 | Aramaki et al. ............. 252/62.3 |
| 2004/0118520 | A1 | 6/2004 | Nakayama et al. ...... 156/345.41 |
| 2005/0202348 | A1 | 9/2005 | Nakayama et al. ........... 430/311 |
| 2006/0081880 | A1 | 4/2006 | Miyazaki et al. ............. 257/200 |
| 2006/0113523 | A1 | 6/2006 | Kubota et al. ................. 257/40 |
| 2006/0214159 | A1 | 9/2006 | Nakayama et al. ............ 257/40 |
| 2007/0012914 | A1 | 1/2007 | Miura et al. .................. 257/40 |
| 2007/0051947 | A1 | 3/2007 | Nakayama et al. ............ 257/40 |
| 2007/0085072 | A1 | 4/2007 | Masumoto et al. ............ 257/40 |
| 2007/0096079 | A1 | 5/2007 | Nakayama et al. ............ 257/40 |

FOREIGN PATENT DOCUMENTS

| EP | 0 428 214 | 5/1991 |
| EP | 0 716 459 | 6/1996 |
| JP | 3-194560 | 8/1991 |
| JP | 8-228034 | 9/1996 |
| JP | 2004-323376 | 11/2004 |

OTHER PUBLICATIONS

P. T. Herwig, et al., "A Soluble Pentacene Precursor: Synthesis, Solid-State Conversion into Pentacene and Application in a Field-Effect Transistor", Advanced Materials, vol. 11, No. 6, 1999, pp. 480-483.

W. Nakwaski, et al., "Temperature Profiles in Etched-Well Surface-Emitting Semiconductor Lasers", Japanese Journal of Applied Physics, vol. 30, No. 4A, Apr. 1991, pp. 596-598.

H. Sirringhaus, et al., "Two-dimensional charge transport in self-organized, high-mobility conjugated polymers", Nature, vol. 401, Oct. 14, 1999, pp. 685-688.

*Primary Examiner*—Bradley W. Baumeister
*Assistant Examiner*—Matthew W Such
(74) *Attorney, Agent, or Firm*—Fitzpatrick, Cella, Harper & Scinto (57) ABSTRACT

Provided is a field effect transistor having an organic semiconductor layer, in which the organic semiconductor layer contains at least a tetrabenzo copper porphyrin crystal and has peaks at two or more of Bragg angles (2θ) in CuKα X-ray diffraction of 8.4°±0.2°, 10.2°±0.2°, 11.8°±0.2°, and 16.9°±0.2°, and the tetrabenzo copper porphyrin crystal comprises a compound represented by the following general formula (1).

General Formula (1):

(Wherein $R_2$'s each represent a hydrogen atom, a halogen atom, a hydroxyl group, or an alkyl group, oxyalkyl group, thioalkyl group, or alkylester group having 1 to 12 carbon atoms, and $R_3$'s each represent a hydrogen atom or an aryl group.).

2 Claims, 3 Drawing Sheets

FIELD EFFECT TRANSISTOR AND METHOD OF MANUFACTURING THE SAME

This application is a divisional of Application Ser. No. 10/545,398, which was the National Stage of International Application No. PCT/JP2004/012044, filed Aug. 17, 2004. The contents of each of the foregoing applications is incorporated herein by reference.

TECHNICAL FIELD

The present invention relates to a field effect transistor having an organic semiconductor layer using a tetrabenzo copper porphyrin crystal and a method of manufacturing the field effect transistor.

BACKGROUND ART

The nonlinear optical characteristics, conductivity, and semiconductivity of an organic semiconductor compound have attracted attention in the field of optoelectronics, so that the development of various devices has been vigorously conducted.

In recent years, a field effect transistor (FET) element using an organic semiconductor compound for its semiconductor layer has been attracting attention. In view of this circumstance, an organic semiconductor compound is now considered to be suitable for the preparation of a flexible element using plastics as its substrate because the organic semiconductor compound exhibits flexible film property as compared to an inorganic material such as silicon.

Representative examples of such an organic semiconductor compound include phthalocyanine-based compounds and polyacenes. Characteristics such as nonlinear optical characteristics, conductivity, and semiconductivity necessary for preparing devices using those compounds as organic materials are known to largely depend on the crystallinity and orientation of the materials as well as their purities. However, it has been difficult to make many compounds such as the phthalocyanine-based compound and the polyacenes mentioned earlier, in which π conjugated systems are extended, highly pure partly because the compounds are insoluble in solvents and susceptible to oxidation in the atmosphere. Moreover, a large-scale apparatus has been necessary for film formation partly because vacuum evaporation should be performed in order to obtain a crystallized film having high orientation.

For instance, pentacene, a representative example of an organic semiconductor compound, can be formed into a film on a substrate by means of vacuum evacuation alone because pentacene has high crystallinity and is insoluble in a solvent.

Meanwhile, a FET is prepared more simply by forming a thin film using a solution of an organic semiconductor that is soluble in an organic solvent by means of a coating method such as a spin coating method. Examples of such a FET include one using a π-conjugated polymer for its semiconductor layer (see "Japanese Journal of Applied Physics", Japan Society of Applied Physics, vol. 30, pp. 596-598, 1991). It is known that, in the case of a π-conjugated polymer, an arrangement state of molecular chains largely affect electric conductive characteristics.

Similarly, it has been reported that a field effect mobility of a π-conjugated polymer field effect transistor is largely dependent on the arrangement state of the molecular chains in the semiconductor layer (see "Nature", Nature Publishing Group, vol. 401, pp. 0.685-687, 1999).

However, the arrangement of the molecular chains of a π-conjugated polymer is performed during a period from solution coating to solution drying. Therefore, there is a possibility that the arrangement state of the molecular chains varies to a large extent owing to an environmental change or depending on coating method. In view of this, there has been reported a FET using a film obtained by: forming a thin film of a soluble precursor of pentacene through coating; and subjecting the thin film to heat treatment to transform the precursor into pentacene (see "Advanced Materials", WILEY-VCH Verlag GmbH, vol. 11, pp. 480-483, 1999). In this case, the transformation into pentacene necessitates high-temperature treatment, and an eliminated component having a large mass must be removed under reduced pressure.

As described above, a conventional FET element using an organic semiconductor compound has required a complicated step such as vacuum film formation, or involved a problem in that the element is easily affected by the environment.

DISCLOSURE OF THE INVENTION

The present invention has been made in order to solve the above problems, and therefore an object of the present invention is to provide a field effect transistor which can be manufactured by a method much simpler than a conventional method and which exhibits a high field effect mobility, and to provide a method of manufacturing the field effect transistor.

That is, according to one aspect of the present invention, there is provided a field effect transistor having an organic semiconductor layer, in which the organic semiconductor layer contains at least a tetrabenzo copper porphyrin crystal and has peaks at two or more of Bragg angles (2θ) in CuKα X-ray diffraction of 8.4°±0.2°, 10.2°±0.2°, 11.8°±0.2°, and 16.9°±0.2°.

In further aspect of the field effect transistor, the tetrabenzo copper porphyrin crystal comprises a compound represented by the following general formula (1).

General Formula (1):

(Wherein $R_2$'s each independently represent at least one kind selected from the group consisting of a hydrogen atom, a halogen atom, a hydroxyl group, and an alkyl group, oxyalkyl group, thioalkyl group, or alkylester group having 1 to 12 carbon atoms, and $R_3$'s represent at least one kind selected from the group consisting of a hydrogen atom and an aryl group.)

In further aspect of the field effect transistor, the tetrabenzo copper porphyrin crystal is obtained by heating a compound represented by the following general formula (2).

General Formula (2):

(Wherein $R_1$'s and $R_2$'s each independently represent at least one kind selected from the group consisting of a hydrogen atom, a halogen atom, a hydroxyl group, and an alkyl group, oxyalkyl group, thioalkyl group, or alkylester group having 1 to 12 carbon atoms, and $R_3$'s represent at least one kind selected from the group consisting of a hydrogen atom and an aryl group.)

In the compound represented by the general formula (2), 8 kinds of isomers can be present depending on whether a double bond of a bicyclo ring is present above or below a porphyrin ring plane. However, a mixing ratio of the isomers is arbitrary.

According to another aspect of the present invention, there is provided a method of manufacturing a field effect transistor having an organic semiconductor layer, including the step of forming the organic semiconductor layer containing at least a tetrabenzo copper porphyrin crystal and having peaks at two or more of Bragg angles (2θ) in CuKα X-ray diffraction of 8.4°±0.2°, 10.2°±0.2°, 11.8°±0.2°, and 16.9°±0.2°, in which the step of forming the organic semiconductor layer is performed by heating a thin film comprising a compound represented by the general formula (2) to produce the tetrabenzo copper porphyrin crystal.

According to the present invention, there can be provided a field effect transistor exhibiting a high field effect mobility.

In addition, according to the present invention, there can be provided a method of manufacturing a field effect transistor exhibiting a high field effect mobility, with which an organic semiconductor layer can be formed much simply than a conventional method.

BEST MODE FOR CARRYING OUT THE INVENTION

Hereinafter, an embodiment of the present invention will be described in detail.

A field effect transistor of the present invention is characterized in that an organic semiconductor layer is used, which contains at least a tetrabenzo copper porphyrin crystal and has peaks at two or more of Bragg angles (2θ) in CuKα X-ray diffraction of 8.4°±0.2°, 10.2°±0.2°, 11.8°±0.2°, and 16.9°±0.2°.

The tetrabenzo copper porphyrin crystal has a structure represented by the following general formula (1) and can be obtained by heating a compound represented by the following general formula (2).

General Formula (1):

(Wherein $R_2$'s each independently represent at least one kind selected from the group consisting of a hydrogen atom, a halogen atom, a hydroxyl group, and an alkyl group, oxyalkyl group, thioalkyl group, or alkylester group having 1 to 12 carbon atoms, and $R_3$'s represent at least one kind selected from the group consisting of a hydrogen atom and an aryl group.)

General Formula (2):

(Wherein $R_1$'s and $R_2$'s each independently represent at least one kind selected from the group consisting of a hydrogen atom, a halogen atom, a hydroxyl group, and an alkyl group, oxyalkyl group, thioalkyl group, or alkylester group having 1 to 12 carbon atoms, and $R_3$'s represent at least one kind selected from the group consisting of a hydrogen atom and an aryl group.)

In the compound represented by the general formula (2), 8 kinds of isomers can be present depending on whether a double bond of a bicyclo ring is present above or below a porphyrin ring plane. However, a mixing ratio of the isomers is arbitrary.

The field effect transistor using an organic semiconductor layer, the semiconductor layer containing at least a tetrabenzo copper porphyrin crystal and having peaks at two or more of Bragg angles (2θ) in CuKα X-ray diffraction of 8.4°±0.2°, 10.2°±0.2°, 11.8°±0.2°, and 16.9°±0.2°, can be manufactured by a method much simpler than a conventional method and exhibits a high mobility.

The X-ray diffraction measurement of the present invention was performed by using a CuKα ray under the following conditions.

Sample: prepared by forming a thin film containing a tetrabenzo copper porphyrin crystal into a substrate by a method described in Examples Machine used: RAD-RX wide angle X-ray diffraction instrument manufactured by Rigaku Corporation
X-ray tube: Cu
Tube voltage: 50 kV
Tube current: 150 mA
Scanning method: 2θ/θ scan
Sampling interval: 0.02 deg.
Integrating time: 1 s
Number of times of integration: 14 times
Measurement temperature: room temperature (20° C.)

The present invention will be described in more detail.

In the present invention, substituents $R_1$'s bound to bicyclooctaene rings of a bicycloporphyrin compound represented by the general formula (2) (hereinafter, referred to as bicyclo compound) are eliminated as $R_1$—CH=CH—$R_1$, when the compound is transformed into a tetrabenzo porphyrin compound represented by the general formula (1) (hereinafter, referred to as benzo compound) through heat treatment.

Therefore, $R_1$'s have only to be each independently at least one kind selected from the group consisting of a hydrogen atom, a halogen atom, a hydroxyl group, and an alkyl group, oxyalkyl group, thioalkyl group, or alkylester group having 1 to 12 carbon atoms, and two or more kinds of them may be combined. If the number of carbon atoms exceeds 12, an eliminated component has an increased molecular weight, so that the eliminated component remains in a benzo compound film, thereby making it impossible to obtain sufficient semiconductor characteristics. $R_1$'s are most preferably hydrogen atoms.

Substituents $R_2$'s of the bicyclo compound represented by the general formula (2) remain as substituents even in the benzo compound represented by the general formula (1) obtained after the heat treatment. Therefore, the substituents $R_2$'s affect the orientation of the benzo compound. $R_2$'s have only to be each independently at least one kind selected from the group consisting of a hydrogen atom, a halogen atom, a hydroxyl group, and an alkyl group, oxyalkyl group, thioalkyl group, or alkylester group having 1 to 12 carbon atoms, and two or more kinds of them may be combined. If the number of carbon atoms in an $R_2$ exceeds 12, an existence of a porphyrin ring with respect to the entire molecule lowers, so that the porphyrin rings are hardly oriented, thereby making it impossible to obtain sufficient semiconductor characteristics. $R_2$'s are most preferably hydrogen atoms. In this case, the stacking of the porphyrin rings occurs more easily, so that film crystallinity increases.

A preferable method of preparing an organic semiconductor layer involves: dissolving a bicyclo compound into an organic solvent; coating a substrate with the solution; and heating the solution to obtain a crystallized film of a benzo compound.

An organic solvent used for dissolving a bicyclo compound is not particularly limited as long as the bicyclo compound does not react with the organic solvent and the bicyclo compound is not precipitated in the organic solvent. In addition, two or more kinds of organic solvents may be mixed when in use. A halogen solvent is preferably used in view of smoothness of a coating film surface and uniformity of the film thickness. Examples of a halogen solvent include chloroform, methylene chloride, dichloroethane, chlorobenzene, and 1,2-dichloroethylene. The concentration of the solution, which is arbitrarily adjusted depending on a desired film thickness, is preferably 0.01 to 5 wt %.

Examples of a coating method include a spin coating method, a dipping method, a dropping method, an offset, screen, and other printing methods, and an ink jet method. In addition, it is desirable to filter the solution through a membrane filter in advance in order to minimize the mixing of foreign material or the like into a semiconductor layer. This is because the mixing of insoluble matter or foreign material from the outside prevents uniform orientation, thereby causing an increase in off-state current or a reduction in on/off ratio. In addition, the coating film of the bicyclo compound can be predried at a temperature equal to or lower than 130° C.

The coated and formed film of the bicyclo compound is heated to cause a retro Diels-Alder reaction, thereby undergoing a transformation into a benzo compound involving the elimination of $R_1$—CH=CH—$R_1$. Crystal growth due to the stacking of the porphyrin rings occurs simultaneously with the formation of the benzo compound, and hence a crystallized film of the benzo compound can be obtained. In addition, an elimination reaction occurs at a temperature equal to or higher than 150° C. A heating temperature for obtaining a higher field effect mobility is desirably in the range of 170 to 280° C., preferably 200 to 230° C. A heating temperature of lower than 170° C. cannot provide a crystallized film having undergone sufficient crystal growth whereas a heating temperature in excess of 280° C. develops a crack owing to abrupt film contraction.

The heating of the film is performed on a hot plate, or in an oven with internal air circulation or a vacuum oven. It is preferable to instantaneously heat the film on a hot plate in order to obtain uniform orientation.

In addition, in order to obtain higher crystallinity, it is preferable to perform rubbing treatment in which a coating film before being heated is lightly rubbed with cloth or the like. Examples of the cloth to be used for the rubbing treatment include, but not limited to, rayon, cotton, and silk.

An organic semiconductor layer using an orientation film of a benzo compound obtained through those operations has an average thickness of 10 to 200 nm, preferably 20 to 100 nm. The term "average thickness" as used herein refers to an average value for film thicknesses measured by using a surface roughness tester or a step-difference measuring apparatus.

Figure 4:
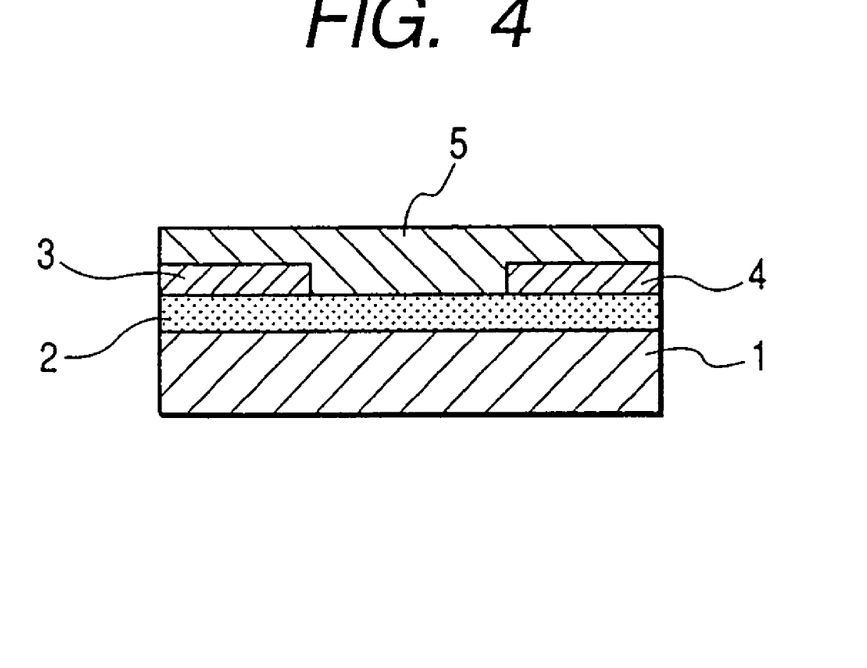
FIG. 4 is an enlarged schematic diagram of a part of a field effect transistor of the present invention.
Figure 5:
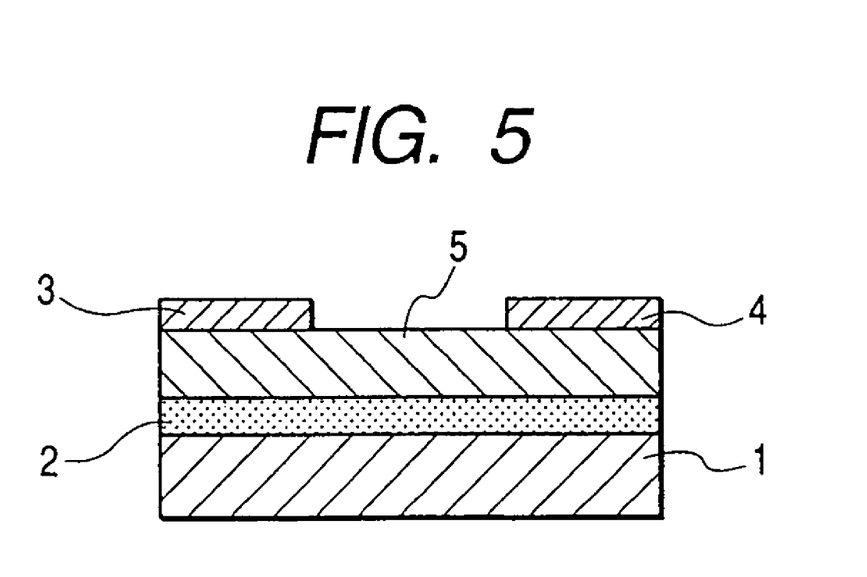
FIG. 5 is an enlarged schematic diagram of a part of a field effect transistor of the present invention.

FIG. 4 and FIG. 5 are each an enlarged schematic diagram of a part of a field effect transistor of the present invention. The field effect transistor of the present invention is constituted of a gate electrode 1, a gate insulating layer 2, a source electrode 3, a drain electrode 4, and an organic semiconductor layer 5.

The gate electrode, the source electrode, and the drain electrode are not particularly limited as long as they are made of conductive materials. Examples of materials for those electrodes include: platinum, gold, silver, nickel, chromium, copper, iron, tin, antimonial lead, tantalum, indium, aluminum, zinc, and magnesium, and alloys thereof; conductive metal oxides such as an indium tin oxide; and inorganic and organic semiconductors with conductivities increased by doping or the like such as a silicon single crystal, polysilicon, amorphous silicon, germanium, graphite, polyacetylene, polyparaphenylene, polythiophene, polypyrrole, polyaniline, polythienylene vinylene, and polyparaphenylene vinylene. Examples of a method of preparing an electrode include a sputtering method, an evaporation method, a printing method using a solution or paste, and an ink jet method. Of the electrode materials listed above, an electrode material having a low electrical resistance at a contact surface with the semiconductor layer is preferable.

Any gate insulating layer can be used as long as the layer can be uniformly coated with a bicyclo compound solution. However, a gate insulating layer having a high dielectric constant and a low conductivity is preferable. Examples of an insulating material for such an insulating layer include: inorganic oxides and nitrides such as silicon oxide, silicon nitride, aluminum oxide, titanium oxide, and tantalum oxide; and organic polymers such as polyacrylate, polymethacrylate, polyethylene terephthalate, polyimide, polyether, and a siloxane polymer. In addition, of the above insulating materials, an insulating material having high surface smoothness is preferable.

To improve coating film uniformity of the bicyclo compound solution on the insulating layer, or to make the orientation of the film of the benzo compound uniform by heating, only the insulating layer surface can be modified. Examples of a modification method include: dry treatment using ozone, plasma, or hexamethyldisilazane gas; and wet treatment using a solution prepared by dissolving tetraalkoxysilane, trichlorosilane, or a surfactant into an organic solvent.

A field effect transistor structure in the present invention may be any one of a top contact electrode type and a bottom contact electrode type. In addition, the field effect transistor structure in the present invention is not limited to a thin film type but may be a stereo type.

Synthesis examples and examples are shown below. However, the present invention is not limited to these examples.

SYNTHESIS EXAMPLE 1

Synthesis of Bicyclo Compound

Step (1)
A mixed solution of 3.16 g (39.5 mmol) of 1,3-cyclohexadiene, 10.5 g (34.1 mmol) of trans-1,2-bis(phenylsulfonyl)ethylene, and 200 ml of toluene was refluxed for 7 hours. Then, the mixed solution was cooled and concentrated under reduced pressure to yield a reaction mixture. The reaction crude product was recrystallized (chloroform/hexane) to yield 5,6-bis(phenylsulfonyl)-bicyclo[2,2,2]octa-2-ene (13.8 g, 35.6 mmol, 90% yield).

Step (2)
A reaction system of a mixed solution of 7.76 g (20 mmol) of the resultant 5,6-bis(phenylsulfonyl)-bicyclo[2,2,2]octa-2-ene and 50 ml of anhydrous tetrahydrofuran was replaced with nitrogen. Then, 2.425 ml (22 mmol) of ethyl isocyanoacetate were added to the mixed solution, and the whole was cooled to 0° C. Potassium tert-butoxide (50 ml/1 M THF solution) was dropped into the mixture in 2 hours, and the whole was stirred at room temperature for 3 hours. After the completion of the reaction, diluted hydrochloric acid was added to the reaction mixture. Then, the reaction mixture was washed with a saturated aqueous solution of sodium hydrogen carbonate, distilled water, and a saturated salt solution in this order, and was dried with anhydrous sodium sulfate. The dried product was purified by means of silica gel column chromatography (chloroform) to yield ethyl-4,7-dihydro-4,7-ethano-2H-isoindole-1-carboxylate (3.5 g, 16 mmol, 80% yield).

Step (3)
Under an argon atmosphere, a mixed solution of 0.42 g (1.92 mmol) of the resultant ethyl-4,7-dihydro-4,7-ethano-2H-isoindole-1-carboxylate and 50 ml of anhydrous THF was cooled to 0° C. Then, 0.228 g (6 mmol) of lithium aluminum hydride powder was added to the mixed solution, and the whole was stirred for 2 hours. After that, THF was removed, and then the remainder was extracted with chloroform, washed with a saturated aqueous solution of sodium hydrogen carbonate, distilled water, and a saturated salt solution in this order, and dried with anhydrous sodium sulfate. The reaction solution was filtered, replaced with argon, and shaded. Then, 10 mg of p-toluenesulfonic acid were added to the reaction solution, and the whole was stirred for 12 hours at room temperature. Furthermore, 0.11 g of p-chloranil was added to the mixture, and the whole was stirred for 12 hours at room temperature. The resultant was washed with a saturated aqueous solution of sodium hydrogen carbonate, distilled water, and a saturated salt solution in this order, and dried with anhydrous sodium sulfate. After the concentration of the solution, the concentrated product was subjected to alumina column chromatography (chloroform) and recrystallized (chloroform/methanol) to yield a metal-free bicyclo compound (bicycloporphyrin) represented by the following structural formula (3) (0.060 g, 0.097 mmol, 20% yield).

(3)

Step (4)
A solution of 0.02 g (0.032 mmol) of bicycloporphyrin and 0.019 g (0.1 mmol) of copper (II) acetate monohydrate in a mixture of 30 ml of chloroform and 3 ml of methanol was stirred at room temperature for 3 hours. The reaction solution was washed with distilled water and a saturated salt solution, and was then dried with anhydrous sodium sulfate. After the concentration of the solution, the concentrated product was recrystallized with chloroform/methanol to yield a bicyclo compound (bicycloporphyrin copper complex) represented by the following structural formula (4) (0.022 g, 100% yield).

(4)

EXAMPLE 1

FIG. 4 shows the structure of a bottom gate type field effect transistor in this example.

First, a highly doped N-type silicon substrate was provided as the gate electrode 1. A silicon oxide film of 5,000 Å in thickness obtained by thermal oxidation of the silicon substrate surface layer was provided as the insulating layer 2. Chromium and gold were deposited from the vapor in this order onto the insulating layer 2 to form the source electrode 3 and the drain electrode 4 by means of an ordinary photolithography technique. Subsequently, the substrate surface was treated with ozone. Then, a coating film made from a 1 wt % chloroform solution of the bicyclo compound synthesized in Synthesis Example 1 was formed on the substrate by means of a spin coating method. Furthermore, the substrate was heated at 220° C. to form the organic semiconductor layer 5 composed of a benzo compound represented by the following structural formula (5). The organic semiconductor layer had an average thickness of 50 nm.

(5)

Figure 3:
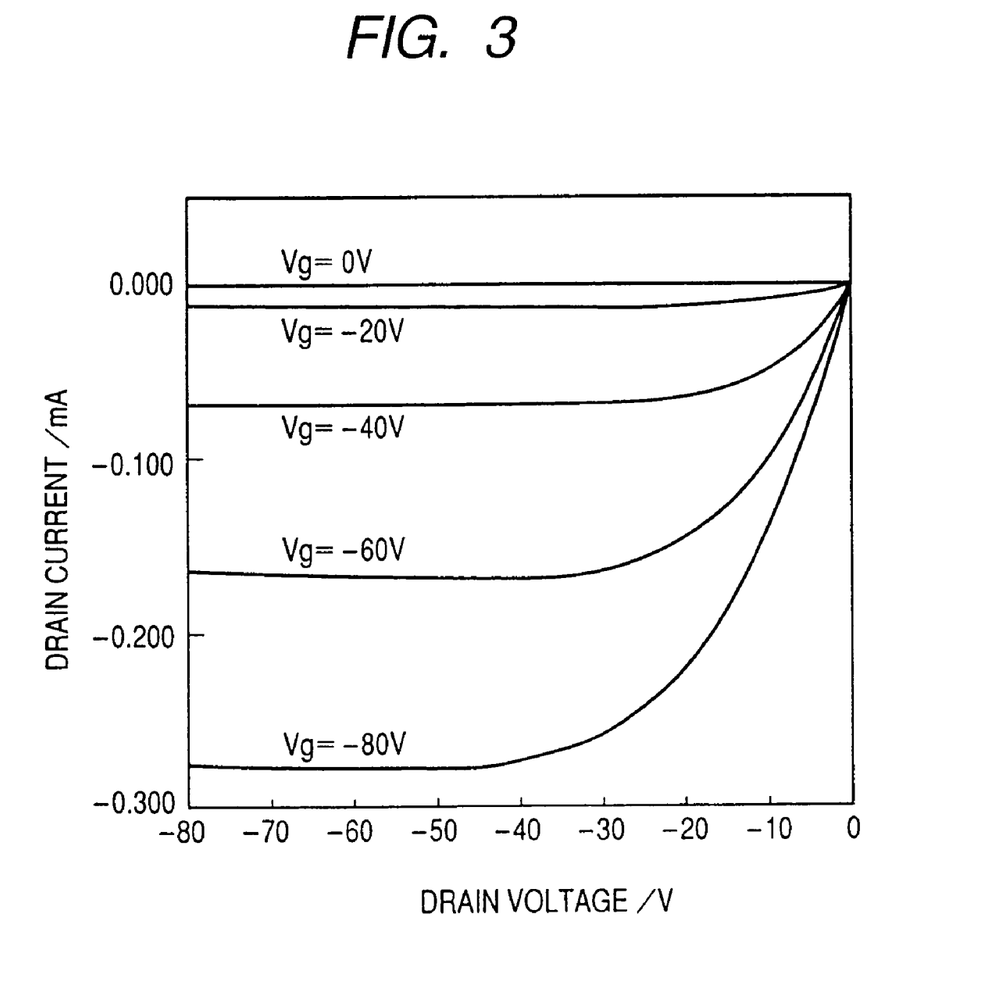
FIG. 3 shows electrical characteristics of a field effect transistor in Example 1 of the present invention.

A field effect transistor having a channel length L of 50 μm and a channel width W of 10 mm was prepared according to the above procedure. The $V_d$-$I_d$ and $V_g$-$I_d$ curves of the prepared transistor were measured by using a Parameter Analyzer 4156C (trade name) manufactured by Agilent, to thereby provide results shown in FIG. 3.

A mobility μ (cm$^2$/Vs) was calculated from the following equation (1).

$$I_d = \mu(C_i W/2L) \times (V_g - V_{th})^2 \qquad \text{(Eq. 1)}$$

In the equation, $C_i$ denotes a capacitance per unit area (F/cm$^2$) of a gate insulating film, and W and L denote the channel width (mm) and the channel length (μm) described in this example, respectively. In addition, $I_d$, $V_g$, and $V_{th}$ denote a drain current (A), a gate voltage (V), and a threshold voltage (V), respectively.

Figure 1:
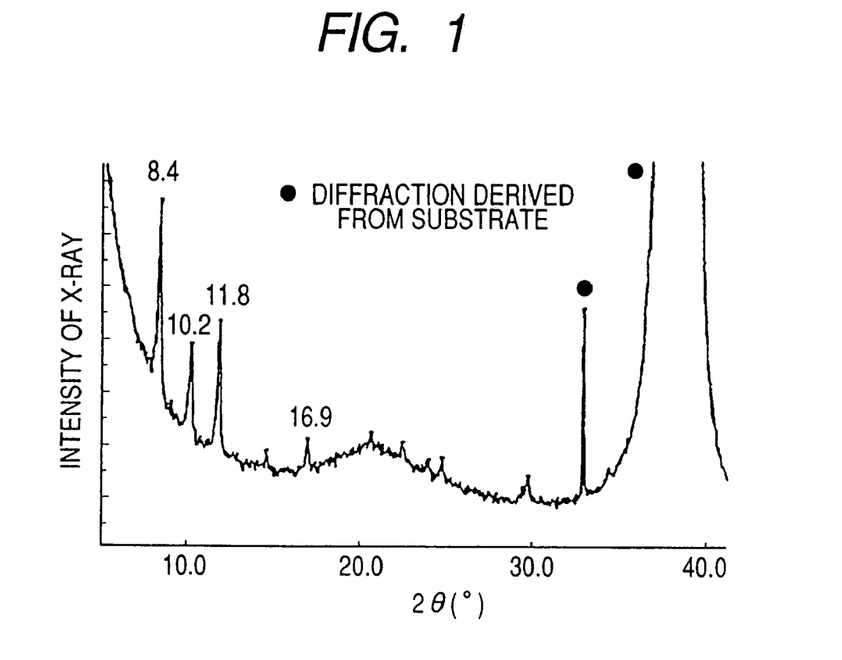
FIG. 1 is an X-ray diffraction pattern of a transistor substrate obtained in Example 1 of the present invention.

Table 1 shows the results. Furthermore, the prepared transistor substrate was subjected to CuKα X-ray diffraction under the above conditions. FIG. 1 shows the results.

Figure 2:
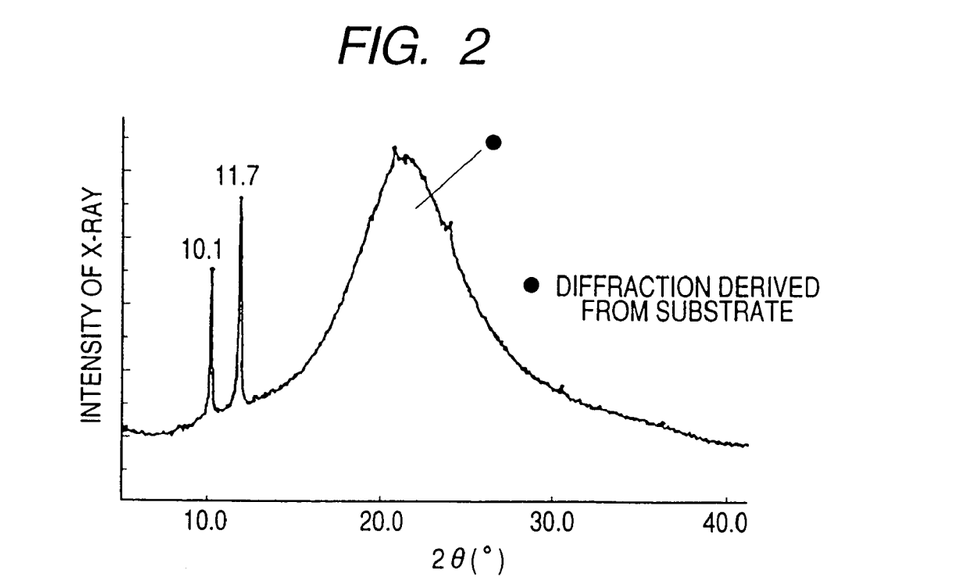
FIG. 2 is an X-ray diffraction pattern of a quartz substrate obtained in Example 1 of the present invention.

Furthermore, a benzo compound was prepared under the above conditions on a quartz substrate and subjected to CuKα X-ray diffraction as above. FIG. 2 shows the results.

EXAMPLE 2

Operations similar to those of Example 1 were performed except that the channel length L and the channel width W were changed to 50 μm and 2 mm, respectively. Table 1 shows the results. In addition, CuKα X-ray diffraction was performed under the conditions of Example 1 to provide similar diffraction.

EXAMPLE 3

Operations similar to those of Example 1 were performed except that the transistor structure was changed to a top electrode type field effect transistor as described below.

FIG. 5 shows the structure of a top electrode type field effect transistor.

First, a highly doped N-type silicon substrate was provided as the gate electrode 1. A silicon oxide film of 5,000 Å in thickness obtained by thermal oxidation of the silicon substrate surface layer was provided as the gate insulating layer 2. Subsequently, the substrate surface was treated with ozone. Then, a coating film made from a 1 wt % chloroform solution of the bicyclo compound synthesized in Synthesis Example 1 was formed on the substrate by means of a spin coating method. Furthermore, the substrate was heated at 220° C. to form the organic semiconductor layer 5 composed of a benzo compound. The organic semiconductor layer on the substrate had an average thickness of 50 nm. Chromium and gold were deposited from the vapor in this order onto the organic semiconductor layer 5 to form the source electrode 3 and the drain electrode 4 with a channel length L of 50 μm and a channel width W of 10 mm by means of an ordinary photolithography technique. Table 1 shows the results. In addition, CuKα X-ray diffraction was performed under the conditions of Example 1 to provide similar diffraction.

EXAMPLE 4

Operations similar to those of Example 3 were performed except that the channel length L and the channel width W were changed to 50 μm and 2 mm, respectively. Table 1 shows the results. In addition, CuKα X-ray diffraction was performed under the conditions of Example 1 to provide similar diffraction.

TABLE 1

|  | W (mm)/L (μm) | Mobility (cm$^2$/Vs) | ON/OFF ratio |
| --- | --- | --- | --- |
| Example 1 | 10/50 | 0.09 | 1.5 × 10$^4$ |
| Example 2 | 2/50 | 0.09 | 1.3 × 10$^4$ |
| Example 3 | 10/50 | 0.09 | 1.7 × 10$^4$ |
| Example 4 | 2/50 | 0.10 | 1.6 × 10$^4$ |

The field effect transistor of the present invention can be used for various devices in the fields of organic electronics and optoelectronics because of its high field effect mobility.

In addition, with the method of manufacturing a field effect transistor of the present invention, an organic semiconductor layer can be formed much simply than a conventional method, and the method can be used for manufacturing a field effect transistor exhibiting a high field effect mobility.

This application claims priority from Japanese Patent Application No. 2003-305487 filed on Aug. 28, 2003, which is hereby incorporated by reference herein.

The invention claimed is:

1. A field effect transistor comprising a gate electrode, a gate insulating layer which is in contact with the gate electrode, an organic semiconductor layer which is in contact with the gate insulating layer, and a source electrode and gate electrode which are in contact with the organic semiconductor layer, wherein the organic semiconductor layer contains at least a tetrabenzo copper porphyrin crystal and at two or more of Bragg angles (2θ) in CuKα X-ray diffraction of 8.4°±0.2°, 10.2°±0.2°, 11.8°±0.2°, and 16.9°±0.2°.

2. The field effect transistor according to claim 1, wherein the tetrabenzo copper porphyrin crystal comprises a compound represented by the following general formula (1)

General Formula (1):

wherein $R_2$'s each independently represent at least one kind selected from the group consisting of a hydrogen atom, a halogen atom, a hydroxyl group, and an alkyl group, oxyalkyl group, thioalkyl group, or alkylester group having 1 to 12 carbon atoms, and $R_3$'s represent at least one kind selected from the group consisting of a hydrogen atom and an aryl group.

* * * * *

UNITED STATES PATENT AND TRADEMARK OFFICE
CERTIFICATE OF CORRECTION

PATENT NO.        : 7,394,096 B2                                    Page 1 of 1
APPLICATION NO. : 11/892326
DATED             : July 1, 2008
INVENTOR(S)       : Daisuke Miura et al.

It is certified that error appears in the above-identified patent and that said Letters Patent is hereby corrected as shown below:

COLUMN 1:
        Line 58, Close up right margin;
        Line 59, Close up left margin; and
        Line 63, "pp. 0.685-687," should read -- pp. 685-687, --.

COLUMN 3:
        Line 52, "much" should read -- much more --.

COLUMN 5:
        Line 42, Close up right margin; and
        Line 43, Close up left margin.

COLUMN 6:
        Line 56, "but" should read -- but are --.

COLUMN 11:
        Line 7, "much" should read -- much more -; and
        Line 24, "and" should read -- and has peaks --.

Signed and Sealed this

Third Day of March, 2009

JOHN DOLL
*Acting Director of the United States Patent and Trademark Office*